US007851490B2

(12) United States Patent
Larsen et al.

(10) Patent No.: US 7,851,490 B2
(45) Date of Patent: Dec. 14, 2010

(54) BENZIMIDAZOLE DERIVATIVES AND THEIR USE FOR MODULATING THE GABA$_A$ RECEPTOR COMPLEX

(75) Inventors: Janus S. Larsen, Holbæk (DK); Lene Teuber, Væløse (DK); Philip K. Ahring, Bagsværd (DK); Elsebet Østergaard Nielsen, København (DK); Naheed Mirza, Birkerød (DK)

(73) Assignee: Neurosearch A/S, Ballerup (DK)

( * ) Notice: Subject to any disclaimer, the term of this patent is extended or adjusted under 35 U.S.C. 154(b) by 439 days.

(21) Appl. No.: 11/887,780

(22) PCT Filed: Apr. 7, 2006

(86) PCT No.: PCT/EP2006/061417

§ 371 (c)(1),
(2), (4) Date: Oct. 3, 2007

(87) PCT Pub. No.: WO2006/108800

PCT Pub. Date: Oct. 19, 2006

(65) Prior Publication Data

US 2009/0036493 A1  Feb. 5, 2009

(30) Foreign Application Priority Data

Apr. 13, 2005  (DK) .............................. 2005 00530

(51) Int. Cl.
*A61K 31/44*  (2006.01)
*C07D 401/02*  (2006.01)

(52) U.S. Cl. ................. 514/339; 546/268.1; 546/268.4; 546/272.7; 546/273.4; 514/336; 514/337

(58) Field of Classification Search ............. 546/268.1, 546/268.4, 272.7, 273.4; 514/336, 337, 339
See application file for complete search history.

(56) References Cited

U.S. PATENT DOCUMENTS

| | | | |
|---|---|---|---|
| 5,360,809 A | | 11/1994 | Axelsson et al. |
| 6,218,547 B1 * | | 4/2001 | Teuber et al. ............ 548/304.4 |
| 6,503,925 B1 * | | 1/2003 | Teuber et al. ................ 514/307 |
| 6,649,609 B2 * | | 11/2003 | Teuber et al. ............. 514/228.2 |
| 6,710,044 B2 * | | 3/2004 | Teuber et al. ............. 514/235.8 |
| 6,936,613 B2 * | | 8/2005 | Teuber et al. ........... 514/252.19 |
| 7,419,995 B2 * | | 9/2008 | Crew et al. .................... 514/394 |
| 7,521,448 B2 * | | 4/2009 | Bolger et al. ............. 514/234.5 |
| 2003/0055055 A1 | | 3/2003 | Teuber et al. |

FOREIGN PATENT DOCUMENTS

| | | |
|---|---|---|
| WO | WO 96/33194 | 10/1996 |
| WO | WO-99-19323 A | 4/1999 |
| WO | WO-02/50057 A1 | 6/2002 |
| WO | WO-2004-087137 A1 | 10/2004 |
| WO | WO-2004/087690 A | 10/2004 |
| WO | WO-2005/040131 A | 5/2005 |
| WO | WO 2006/060381 | 6/2006 |
| WO | WO 2007/110374 | 10/2007 |

* cited by examiner

*Primary Examiner*—Golam M Shameem
(74) *Attorney, Agent, or Firm*—Birch, Stewart, Kolasch & Birch, LLP

(57) ABSTRACT

This invention relates to novel benzimidazole derivatives, pharmaceutical compositions containing these compounds, and methods of treatment therewith.

The compounds of the invention are useful in the treatment of central nervous system diseases and disorders, which are responsive to modulation of the GABA$_A$ receptor complex, and in particular for combating anxiety and related diseases.

8 Claims, No Drawings

BENZIMIDAZOLE DERIVATIVES AND THEIR USE FOR MODULATING THE GABA$_A$ RECEPTOR COMPLEX

TECHNICAL FIELD

This invention relates to novel benzimidazole derivatives, pharmaceutical compositions containing these compounds, and methods of treatment therewith.

The compounds of the invention are useful in the treatment of central nervous system diseases and disorders, which are responsive to modulation of the GABA$_A$ receptor complex, and in particular for combating anxiety and related diseases.

BACKGROUND ART

The modulatory sites on the GABA$_A$ receptor complex, such as for example the benzodiazepine binding site, are the target for anxiolytic drugs, such as the classical anxiolytic benzodiazepines. However, they are associated with a number of undesirable features.

Multiple isoforms of the GABA$_A$ receptor exist; each receptor is a pentameric complex comprising subunits drawn from $\alpha_{1-6}$, $\beta_{1-3}$, $\gamma_{1-3}$, $\delta$, $\epsilon$, and $\theta$ subunit isoforms. The classical anxiolytic benzodiazepines show no subtype selectivity. It has been suggested that one of the key elements in the disadvantages of the classical benzodiazepanes (such as sedation, dependency, and cognitive impairment) is related to the $\alpha 1$ subunit of the GABA$_A$ receptors. Thus compounds with selectivity for the $\alpha 2$ and/or $\alpha 3$ subunits over the $\alpha 1$ subunit are expected to have an improved side effect profile.

Thus, there is still a strong need for compounds with an optimised pharmacological profile. Furthermore, there is a strong need to find effective compounds without unwanted side effects associated with older compounds.

SUMMARY OF THE INVENTION

In its first aspect, the invention provides a compound of the Formula I:

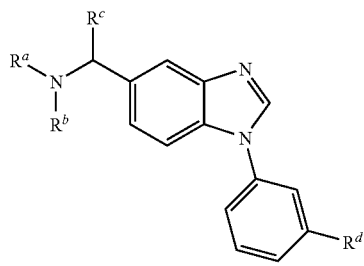

or an N-oxide thereof, any of its isomers or any mixture of its isomers, or a pharmaceutically acceptable salt thereof, wherein $R^a$, $R^b$, $R^c$ and $R^d$ are defined as below.

In its second aspect, the invention provides a pharmaceutical composition, comprising a therapeutically effective amount of a compound of the invention, or an N-oxide thereof, any of its isomers or any mixture of its isomers, or a pharmaceutically acceptable salt thereof, together with at least one pharmaceutically acceptable carrier, excipient or diluent.

In a further aspect, the invention provides the use of a compound of the invention, or an N-oxide thereof, any of its isomers or any mixture of its isomers, or a pharmaceutically acceptable salt thereof, for the manufacture of a pharmaceutical composition for the treatment, prevention or alleviation of a disease or a disorder or a condition of a mammal, including a human, which disease, disorder or condition is responsive to modulation of the GABA$_A$ receptor complex in the central nervous system.

In a still further aspect, the invention relates to a method for treatment, prevention or alleviation of a disease or a disorder or a condition of a living animal body, including a human, which disorder, disease or condition is responsive to modulation of the GABA$_A$ receptor complex in the central nervous system, which method comprises the step of administering to such a living animal body in need thereof a therapeutically effective amount of a compound of the invention, or an N-oxide thereof, any of its isomers or any mixture of its isomers, or a pharmaceutically acceptable salt thereof.

Other objects of the invention will be apparent to the person skilled in the art from the following detailed description and examples.

DETAILED DISCLOSURE OF THE INVENTION

Substituted Benzimidazole Derivatives

In its first aspect the present invention provides a compound of general formula (I):

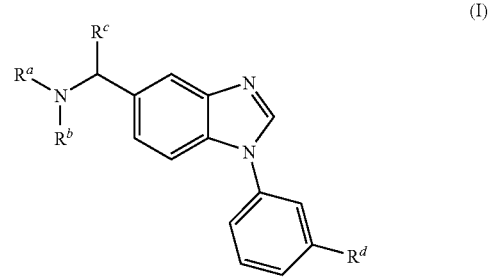

or an N-oxide thereof, any of its isomers or any mixture of its isomers, or a pharmaceutically acceptable salt thereof, wherein $R^a$, $R^b$ and $R^c$ independent of each other represent hydrogen, alkyl, cycloalkyl, cycloalkylakyl, alkenyl, alkynyl, hydroxy, alkoxy, alkoxyalkyl, arylalkyl, formyl, alkylcarbonyl or alkoxyalkylcarbonyl;

$R^d$ represents a heteroaryl group;

which heteroaryl group is optionally substituted with one or more substituents independently selected from the group consisting of:

halo, hydroxy, R'R"N—, R'R"N-alkyl, cyano, nitro, trifluoromethyl, trifluoromethoxy, hydrazino, alkoxy, cycloalkoxy, alkyl, cycloalkyl, cycloalkylalkyl, alkenyl, and alkynyl;

wherein R' and R" independent of each other are hydrogen or alkyl.

In one embodiment, $R^a$ represents hydrogen, alkyl or arylalkyl. In a further embodiment, $R^a$ represents hydrogen or alkyl. In a special embodiment, $R^a$ represents hydrogen. In a further embodiment, $R^a$ represents alkyl, such as methyl or ethyl. In a still further embodiment, $R^a$ represents arylalkyl, such as phenylalkyl, such as benzyl.

In a further embodiment, $R^b$ represents hydrogen, alkyl, alkoxy, arylalkyl, formyl or alkylcarbonyl. In a still further embodiment, $R^b$ represents hydrogen, alkyl, formyl or alkylcarbonyl. In a special embodiment, $R^b$ represents hydrogen. In a further embodiment, $R^b$ represents alkyl, such as methyl or ethyl. In a still further embodiment, $R^b$ represents arylalkyl, such as phenylalkyl, such as benzyl. In a further embodiment, $R^b$ represents formyl or alkylcarbonyl, such as acetyl. In a still further embodiment, $R^b$ represents alkoxy, such as methoxy.

In a still further embodiment, $R^c$ represents hydrogen or alkyl. In a special embodiment, $R^c$ represents hydrogen. In a further embodiment, $R^c$ represents alkyl, such as methyl.

In a further embodiment, $R^d$ represents a heteroaryl group selected from thiazolyl, pyridyl, pyrimidyl and pyrazinyl; which heteroaryl group is optionally substituted with one or more substituents independently selected from the group consisting of: halo, hydrazino and alkoxy.

In a still further embodiment, $R^d$ represents optionally substituted thiazolyl. In a further embodiment, $R^d$ represents thiazolyl, such as thiazol-2-yl. In a still further embodiment, $R^d$ represents halo-thiazolyl, such as chloro-thiazolyl, such as 5-chloro-thiazol-2-yl.

In a still further embodiment, $R^d$ represents optionally substituted pyridyl. In a further embodiment, $R^d$ represents pyridyl, such as pyridin-2-yl or pyridin-3-yl. In a still further embodiment, $R^d$ represents halopyridyl, such as fluoropyridyl, such as 6-fluoro-pyridin-3-yl or 2-fluoro-pyridin-3-yl. In a further embodiment, $R^d$ represents hydrazinopyridyl, such as 6-hydrazino-pyridin-3-yl. In a further embodiment, $R^d$ represents alkoxypyridyl, such as methoxypyridyl, such as 2-methoxy-pyridin-3-yl.

In a still further embodiment, $R^d$ represents optionally substituted pyrimidyl. In a further embodiment, $R^d$ represents pyrimidyl, such as pyrimidin-5-yl. In a still further embodiment, $R^d$ represents dialkoxypyrimidyl, such as dimethoxypyrimidyl, such as 2,4-dimethoxypyrimidin-5-yl In a still further embodiment, $R^d$ represents optionally substituted pyrazinyl. In a further embodiment, $R^d$ represents pyrazinyl, such as pyrazin-2-yl.

In a still further embodiment, $R^a$, $R^b$ and $R^c$ independent of each other represent hydrogen, alkyl, cycloalkyl, cycloalkylalkyl, alkenyl, alkynyl, hydroxy, alkoxy, alkoxyalkyl, formyl, alkylcarbonyl or alkoxyalkylcarbonyl.

In a still further embodiment, $R^d$ represents a heteroaryl group; which heteroaryl group is optionally substituted with one or more substituents independently selected from the group consisting of: halo, hydroxy, R'R"N—, R'R"N-alkyl, cyano, nitro, trifluoromethyl, trifluoromethoxy, alkoxy, cycloalkoxy, alkyl, cycloalkyl, cycloalkylalkyl, alkenyl, and alkynyl; wherein R' and R" independent of each other are hydrogen or alkyl.

In a special embodiment the chemical compound of the invention is

C-[1-(3-Thiazol-2-yl-phenyl)-1H-benzoimidazol-5-yl]-methylamine;

C-[1-(3-Pyridin-3-yl-phenyl)-1H-benzoimidazol-5-yl]-methylamine;

C-[1-(3-[6-Fluoro-pyridin-3-yl]-phenyl)-1H-benzoimidazol-5-yl]-methylamine;

C-[1-(3-[Pyridin-2-yl]-phenyl)-1H-benzoimidazol-5-yl]-methylamine;

C-[1-(3-Pyrazin-2-yl-phenyl)-1H-benzoimidazol-5-yl]-methylamine;

1-[1-(3-Pyrazin-2-yl-phenyl)-1H-benzoimidazol-5-yl]-ethylamine;

1-[1-(3-Pyridin-3-yl-phenyl)-1H-benzoimidazol-5-yl]-ethylamine;

1-{1-[3-(6-Fluoro-pyridin-3-yl)-phenyl]-1H-benzoimidazol-5-yl}-ethylamine;

1-{1-[3-(6-Hydrazino-pyridin-3-yl)-phenyl]-1H-benzoimidazol-5-yl}-ethylamine;

1-[1-(3-Pyrimidin-5-yl-phenyl)-1H-benzoimidazol-5-yl]-ethylamine;

N-[1-(3-Thiazol-2-yl-phenyl)-1H-benzoimidazol-5-ylmethyl]-acetamide;

N-[1-(3-Pyridin-2-yl-phenyl)-1H-benzoimidazol-5-ylmethyl]-acetamide;

N-(1-{1-[3-(2-Fluoro-pyridin-3-yl)-phenyl]-1H-benzoimidazol-5-yl}-ethyl)-formamide;

N-(1-{1-[3-(2-Methoxy-pyridin-3-yl)-phenyl]-1H-benzoimidazol-5-yl}-ethyl)-formamide;

N-(1-{1-[3-(2,4-Dimethoxy-pyrimidin-5-yl)-phenyl]-1H-benzoimidazol-5-yl}-ethyl)-formamide;

1-{1-[3-(2,4-Dimethoxy-pyrimidin-5-yl)-phenyl]-1H-benzoimidazol-5-yl}-ethylamine;

1-{1-[3-(2-Methoxy-pyridin-3-yl)-phenyl]-1H-benzoimidazol-5-yl}-ethylamine;

1-{1-[3-(2-Fluoro-pyridin-3-yl)-phenyl]-1H-benzoimidazol-5-yl}-ethylamine;

Methyl-[1-(3-pyridin-3-yl-phenyl)-1H-benzoimidazol-5-ylmethyl]-amine;

Dimethyl-[1-(3-pyridin-3-yl-phenyl)-1H-benzoimidazol-5-ylmethyl]-amine;

Benzyl-{1-[1-(3-pyridin-3-yl-phenyl)-1H-benzoimidazol-5-yl]-ethyl}-amine;

Dibenzyl-{1-[1-(3-pyridin-3-yl-phenyl)-1H-benzoimidazol-5-yl]-ethyl}-amine;

Methyl-[1-(3-thiazol-2-yl-phenyl)-1H-benzoimidazol-5-ylmethyl]-amine;

Dimethyl-[1-(3-thiazol-2-yl-phenyl)-1H-benzoimidazol-5-ylmethyl]-amine;

Ethyl-[1-(3-thiazol-2-yl-phenyl)-1H-benzoimidazol-5-ylmethyl]-amine;

Diethyl-[1-(3-thiazol-2-yl-phenyl)-1H-benzoimidazol-5-ylmethyl]-amine;

Benzyl-[1-(3-thiazol-2-yl-phenyl)-1H-benzoimidazol-5-ylmethyl]-amine;

Dibenzyl-[1-(3-thiazol-2-yl-phenyl)-1H-benzoimidazol-5-ylmethyl]-amine;

O-Methyl-N-{1-[1-(3-pyridin-3-yl-phenyl)-1H-benzoimidazol-5-yl]-ethyl}-hydroxylamine;

N-{1-[3-Thiazol-2-yl-phenyl]-1H-benzoimidazol-5-ylmethyl}-formamide;

1-{1-[3-(5-Chloro-thiazol-2-yl)-phenyl]-1H-benzoimidazol-5-yl}-ethylamine;

or an N-oxide thereof, any of its isomers or any mixture of its isomers, or a pharmaceutically acceptable salt thereof.

In a further special embodiment the chemical compound of the invention is 1-{1-[3-(5-Chloro-thiazol-2-yl)-phenyl]-1H-benzoimidazol-5-yl}-ethanol; or an N-oxide thereof, any of its isomers or any mixture of its isomers, or a pharmaceutically acceptable salt thereof.

Any combination of two or more of the embodiments as described above is considered within the scope of the present invention.

Definition of Substituents

In the context of this invention halo represents fluoro, chloro, bromo or iodo.

In the context of this invention an alkyl group designates a univalent saturated, straight or branched hydrocarbon chain. The hydrocarbon chain preferably contain of from one to six carbon atoms ($C_{1-6}$-alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises from two to six carbon atoms ($C_{2-6}$-alkenyl), including at least one double bond. In a most preferred embodiment the alkenyl group of the invention is ethenyl; 1- or 2-propenyl; 1-, 2- or 3-butenyl, or 1,3-butadienyl; 1-, 2-, 3-, 4- or 5-hexenyl, or 1,3-hexadienyl, or 1,3,5-hexatrienyl.

In the context of this invention an alkynyl group designates a carbon chain containing one or more triple bonds, including di-ynes, tri-ynes and poly-ynes. In a preferred embodiment the alkynyl group of the invention comprises from two to six carbon atoms ($C_{2-6}$-alkynyl), including at least one triple bond. In its most preferred embodiment the alkynyl group of the invention is ethynyl; 1-, or 2-propynyl; 1-, 2-, or 3-butynyl, or 1,3-butadiynyl; 1-, 2-, 3-, 4-pentynyl, or 1,3-pentadiynyl; 1-, 2-, 3-, 4-, or 5-henynyl, or 1,3-hexadiynyl or 1,3,5-hexatriynyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

Alkoxy means O-alkyl, wherein alkyl is as defined above.

Alkoxyalkyl means alkoxy as above and alkyl as above, meaning for example, methoxymethyl.

Cycloalkoxy means O-cycloalkyl, wherein cycloalkyl is as defined above.

Cycloalkylalkyl means cycloalkyl as above and alkyl as above, meaning for example, cyclopropylmethyl.

In the context of this invention a heteroaryl group designates an aromatic mono- or bicyclic heterocyclic group, which holds one or more heteroatoms in its ring structure. Preferred heteroatoms include nitrogen (N), oxygen (O), and sulphur (S).

Preferred monocyclic heteroaryl groups of the invention include aromatic 5- and 6-membered heterocyclic monocyclic groups, including for example, but not limited to, oxazolyl, isoxazolyl, thiazolyl, isothiazolyl, 1,2,4-oxadiazolyl, 1,2,4-thiadiazolyl, 1,2,5-oxadiazolyl, 1,2,5-thiadiazolyl, imidazolyl, pyrrolyl, pyrazolyl, furanyl, thienyl, pyridyl, pyrimidyl, pyridazinyl or pyrazinyl.

Preferred bicyclic heteroaryl groups of the invention include for example, but not limited to, indolizinyl, indolyl, isoindolyl, indazolyl, benzofuranyl, benzo[b]thienyl, benzimidazolyl, benzoxazolyl, benzothiazolyl, benzo[d]isothiazolyl, purinyl, quinolinyl, isoquinolinyl, cinnolinyl, phthalazinyl, quinazolinyl, quinoxalinyl, 1,8-naphthyridinyl, pteridinyl, and indenyl.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Examples of pharmaceutically acceptable cationic salts of a chemical compound of the invention include, without limitation, the sodium, the potassium, the calcium, the magnesium, the zinc, the aluminium, the lithium, the choline, the lysinium, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound of the invention include examples of suitable prodrugs of the substances according to the invention include compounds modified at one or more reactive or derivatizable groups of the parent compound. Of particular interest are compounds modified at a carboxyl group, a hydroxyl group, or an amino group. Examples of suitable derivatives are esters or amides.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

It will be appreciated by those skilled in the art that the compounds of the present invention may contain one or more chiral centres and that such compounds may exist in different stereoisomeric forms—including enantiomers, diastereomers and cis-trans-isomers.

The invention includes all such isomers and any mixtures thereof including racemic mixtures.

Methods for the resolution of optical isomers, known to those skilled in the art may be used, and will be apparent to the average worker skilled in the art. Such methods include those discussed by J. Jaques, A. Collet, and S. Wilen in "Enantiomers, Racemates, and Resolutions", John Wiley and Sons, New York (1981).

Optical active compounds can also be prepared from optical active starting materials.

N-oxides

In the context of this invention an N-oxide designates an oxide derivative of a nitrogen containing compound, e.g. N-containing heterocyclic compounds capable of forming such N-oxides, and compounds holding one or more amino groups. For example, the N-oxide of a compound containing a pyridyl may be the 1-oxy-pyridin-2-, -3 or -4-yl derivative.

N-oxides of the compounds of the invention may be prepared by oxidation of the corresponding nitrogen base using a conventional oxidizing agent such as hydrogen peroxide in the presence of an acid such as acetic acid at an elevated temperature, or by reaction with a peracid such as peracetic acid in a suitable solvent, e.g. dichloromethane, ethyl acetate or methyl acetate, or in chloroform or dichloromethane with 3-chloroperoxybenzoic acid.

Labelled Compounds

The compounds of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radionuclide as a label. Positron emitting radionuclides are all candidates for usage. In the context of this invention the radionuclide is preferably selected from $^2$H (deuterium), $^3$H (tritium), $^{13}$C, $^{14}$C, $^{131}$I, $^{125}$I, $^{123}$I, and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

The chemical compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

The compounds of this invention may exist in unsolvated as well as in solvated forms with pharmaceutically acceptable solvents such as water, ethanol and the like. In general, the solvated forms are considered equivalent to the unsolvated forms for the purposes of this invention.

Biological Activity

Compounds of the invention are capable of modulating the $GABA_A$ receptor complex. They may be tested for their ability to bind to the $GABA_A$ receptor complex, including specific subunits thereof.

The compounds of the present invention, being ligands for the benzodiazepine binding site on $GABA_A$ receptors, are therefore of use in the treatment and/or prevention of a variety of disorders of the central nervous system. Thus in further aspect, the compounds of the invention are considered useful for the treatment, prevention or alleviation of a disease, disorder or condition responsive to modulation of the $GABA_A$ receptor complex in the central nervous system.

In a special embodiment, the compounds of the invention are considered useful for the treatment, prevention or alleviation of anxiety disorders, such as panic disorder with or without agoraphobia, agoraphobia without history of panic disorder, animal and other phobias including social phobias, obsessive-compulsive disorder, and generalized or substance-induced anxiety disorder;

stress disorders including post-traumatic and acute stress disorder;

sleep disorders;

memory disorder;

neuroses;

convulsive disorders, for example epilepsy, seizures, convulsions, or febrile convulsions in children;

migraine;

mood disorders;

depressive or bipolar disorders, for example depression, single-episode or recurrent major depressive disorder, dysthymic disorder, bipolar disorder, bipolar I and bipolar II manic disorders, and cyclothymic disorder, psychotic disorders, including schizophrenia;

neurodegeneration arising from cerebral ischemia;

attention deficit hyperactivity disorder;

pain and nociception, e.g. neuropathic pain;

emesis, including acute, delayed and anticipatory emesis, in particular emesis induced by chemotherapy or radiation;

motion sickness, post-operative nausea and vomiting;

eating disorders including anorexia nervosa and bulimia nervosa;

premenstrual syndrome;

neuralgia, e.g. trigeminal neuralgia;

muscle spasm or spasticity, e.g. in paraplegic patients;

the effects of substance abuse or dependency, including alcohol withdrawal;

cognitive disorders, such as Alzheimer's disease; and cerebral ischemia, stroke, head trauma;

tinnitus:

disorders of circadian rhythm, e.g. in subjects suffering from the effects of jet lag or shift work.

Preferably the compounds of the invention are considered useful for the treatment, prevention or alleviation of anxiety disorders, such as panic disorder with or without agoraphobia, agoraphobia without history of panic disorder, animal and other phobias including social phobias, obsessive-compulsive disorder, and generalized or substance-induced anxiety disorder;

Further, the compounds of the invention may be useful as radioligands in assays for detecting compounds capable of binding to the human $GABA_A$ receptor.

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

Preferred compounds of the invention show a biological activity in the sub-micromolar and micromolar range, i.e. of from below 1 to about 100 µM.

Pharmaceutical Compositions

In another aspect the invention provides novel pharmaceutical compositions comprising a therapeutically effective amount of the chemical compound of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers, and, optionally, other therapeutic and/or prophylactic ingredients, known and used in the art. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient, which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

In another aspect the invention provides a method for the treatment, prevention or alleviation of a disease or a disorder or a condition of a living animal body, including a human, which disease, disorder or condition is responsive to modulation of the $GABA_A$ receptor complex in the central nervous system, and which method comprises administering to such a living animal body, including a human, in need thereof an effective amount of a chemical compound of the invention.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples, which are not intended to be in any way limiting to the scope of the invention as claimed.

General: All reactions involving air sensitive reagents or intermediates were performed under nitrogen and in anhydrous solvents. Magnesium sulphate or sodium sulphate was used as drying agent in the workup-procedures and solvents were evaporated under reduced pressure.

Example 1

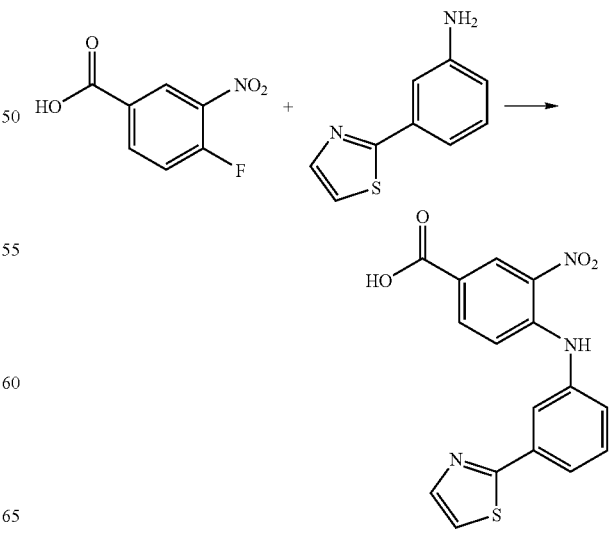

3-Nitro-4-(3-thiazol-2-yl-phenylamino)benzoic acid

To a solution of 3-thiazol-2-yl-phenylamine (14.0 g, 79 mmol) in anhydrous NMP (50 ml) was added 4-fluoro-3-nitrobenzoic acid (15.0 g, 127 mmol). The resultant mixture was stirred at 90° C. over night. The cooled reaction cake was suspended in water and the solid was filtered off, washed with water and dried in the air to afford the desired product (22.5 g, 83%).

3-Nitro-4-(3-bromophenylamino)benzoic acid

This was prepared analogously from 4-fluoro-3-nitrobenzoic acid and 3-bromoaniline.

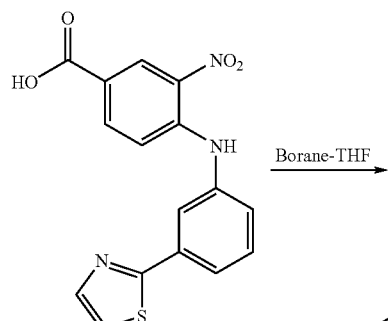

[3-Nitro-4-(3-thiazol-2-yl-phenylamino)-phenyl]-methanol

The above product was dissolved in anhydrous THF (150 ml) in a nitrogen atmosphere. The solution was cooled to 0° C. and a 1M solution of borane-THF complex in THF (132 ml) was added dropwise with stirring. After the addition, the reaction mixture was left with stirring at ambient temperature over night. The solvent was removed in vacuo and the residue was partitioned between water and dichloromethane. The organic layer was dried over magnesium sulfate and evaporated to dryness to leave the desired product (23.3 g, 77%).

[3-Nitro-4-(3-bromophenylamino)phenyl]methanol

This was prepared analogously from 3-nitro-4-(3-bromophenylamino)benzoic acid.

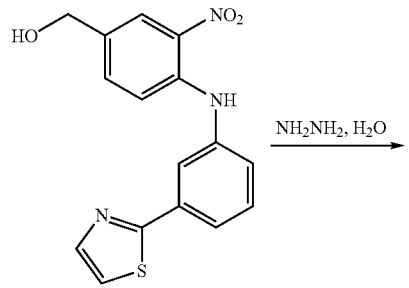

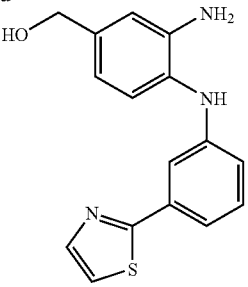

[3-Amino-4-(3-thiazol-2-yl-phenylamino)-phenyl]-methanol

To a solution of the above product (17.8 g, 54.0 mmol) in a mixture of THF (100 ml) and ethanol (50 ml) was added hydrazine hydrate (11 ml, 217 mmol) and a catalytic amount of Raney nickel. The mixture was stirred at ambient conditions over night and then filtered through celite. The filtrate was evaporated to dryness to afford the desired product (15.8 g, 86%).

[3-Amino-4-(3-bromophenylamino)phenyl]methanol

This was prepared analogously from [3-nitro-4-(3-bromophenylamino)phenyl]-methanol.

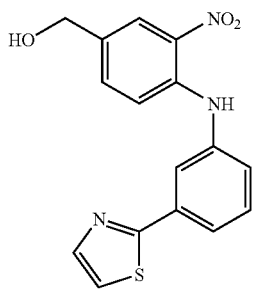

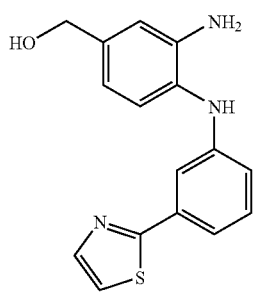

[1-(3-Thiazol-2-yl-phenyl)-1H-benzoimidazol-5-yl]-methanol

To a solution of the above product (15.8 g, 53.1 mmol) in anhydrous THF (100 ml) was added triethyl orthoformate (18 ml, 0.11 mol) and a catalytic amount of p-toluenesulfonic acid. The resultant solution was stirred at reflux for three hours and then the solvent was removed in vacuo. The residue was partitioned between aqueous sodium carbonate and a mixture of ethyl acetate and methanol. The organic layer was dried over sodium sulfate and concentrated in vacuo. Column chromatographic work-up of the concentrate on silica gel, eluting with a mixture of dichloromethane and methanol afforded the desired product (6.5 g, 40%).

[1-(3-Bromophenyl)-1H-benzimidazol-5-yl]methanol

This was prepared analogously from [3-Amino-4-(3-bromophenylamino)phenyl]-methanol.

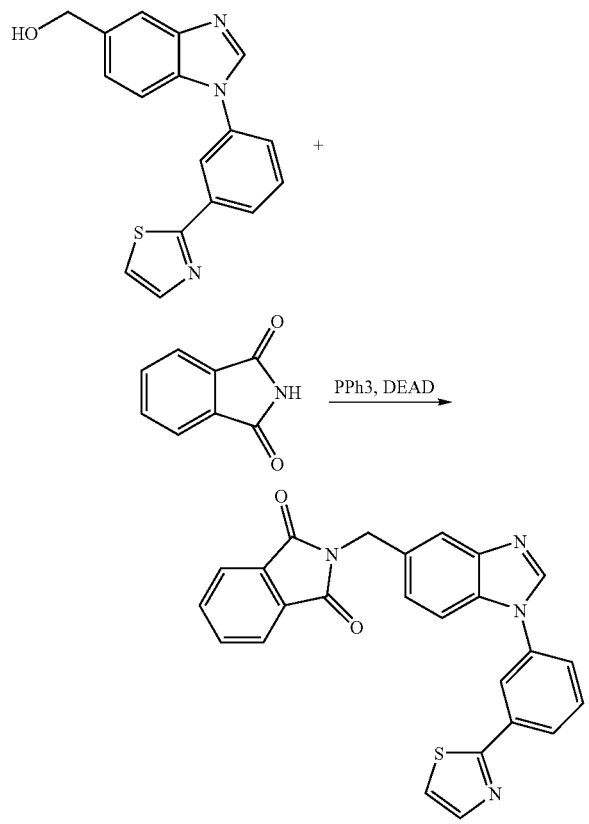

2-[1-(3-Thiazol-2-yl-phenyl)-1H-benzoimidazol-5-ylmethyl]-isoindole-1,3-dione

To an ice-cooled mixture of the above product (6.5 g, 21.1 mmol), phthalimide (3.7 g, 25.4 mmol) and triphenylphosphine in anhydrous THF (150 ml) was added diethylazodicarboxylate (4.2 g, 25.4 mmol) dropwise with stirring over 15 min. Stirring was continued for 30 min. whereafter the solvent was removed in vacuo. The residue was triturated with ethyl acetate and the resultant precipitate was filtered off, washed with ethyl acetate and dried in the air to leave the desired product (7.5 g, 81%).

2-[1-(3-Bromo-phenyl)-1H-benzimidazol-5-ylmethyl]-isoindole-1,3-dione

This was prepared analogously from [1-(3-bromo-phenyl)-1H-benzimidazol-5-yl]methanol.

2-{1-[1-(3-Bromo-phenyl)-1H-benzoimidazol-5-yl]-ethyl}-isoindole-1,3-dione

This was prepared analogously from 1-[1-(3-bromo-phenyl)-1H-benzoimidazol-5-yl]-ethanol.

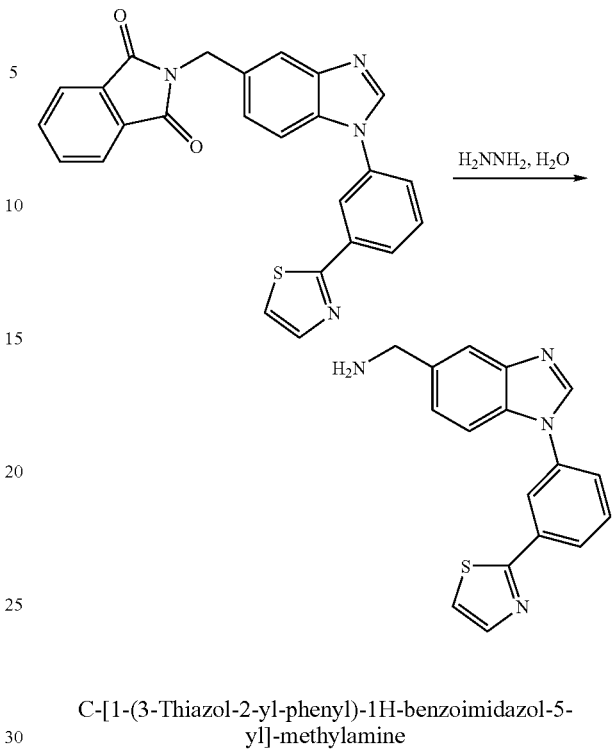

C-[1-(3-Thiazol-2-yl-phenyl)-1H-benzoimidazol-5-yl]-methylamine

To a suspension of the above product (7.5 g, 17.2 mmol) in abs. ethanol (100 ml) was added hydrazine hydrate (3.5 ml 68.7 mmol). The mixture was stirred at reflux for 1 hour and then left at ambient conditions over night. The solvent was removed in vacuo and the residue was triturated with water to leave a solid, which was purified by column chromatography on silica gel, using a mixture of dichloromethane and methanol (9:1 v/v) as the eluent. This afforded the desired product as a white, crystalline solid (3.8 g, 71%). Mp. 99.7° C.

C-[1-(3-Pyridin-3-yl-phenyl)-1H-benzoimidazol-5-yl]-methylamine

This was prepared analogously from 2-[1-(3-(pyridin-3-yl)-phenyl)-1H-benzoimidazol-5-ylmethyl]-isoindole-1,3-dione in 26% yield. Mp. 107-110° C.

C-[1-(3-[6-Fluoro-pyridin-3-yl]-phenyl)-1H-benzoimidazol-5-yl]-methylamine

This was prepared analogously from 2-[1-(3-(6-fluoro-pyridin-3-yl)-phenyl)-1H-benzoimidazol-5-ylmethyl]-isoindole-1,3-dione in 25% yield. Mp. 141-143° C.

C-[1-(3-Pyridin-2-yl-phenyl)-1H-benzoimidazol-5-yl]-methylamine

This was prepared analogously from 2-[1-(3-pyridin-2-yl-phenyl)-1H-benzoimidazol-5-ylmethyl]-isoindole-1,3-dione in 18% yield. Mp. 224-229° C.

C-[1-(3-Pyrazin-2-yl]-phenyl)-1H-benzoimidazol-5-yl]-methylamine

This was prepared analogously from 2-[1-(3-(pyrazin-2-yl)-phenyl)-1H-benzoimidazol-5-ylmethyl]-isoindole-1,3-dione in 22% yield. Mp. 163-165° C.

1-[1-(3-Pyrazin-2-yl-phenyl)-1H-benzoimidazol-5-yl]-ethylamine

This is prepared analogously from 2-[1-[1-(3-(pyrazin-2-yl)-phenyl)-1H-benzoimidazol-5-yl]-ethyl]-isoindole-1,3-dione. LC-ESI-HRMS of [M+H]+ shows 316.155 Da. Calc. 316.15622 Da. dev. −3.9 ppm.

1-[1-(3-Pyridin-3-yl-phenyl)-1H-benzoimidazol-5-yl]-ethylamine

This was prepared analogously from 2-{1-[1-(3-pyridin-3-yl-phenyl)-1H-benzoimidazol-5-yl]-ethyl}-isoindole-1,3-dione in 10% yield. LC-ESI-HRMS of [M+H]+ shows 315.1604 Da. Calc. 315.160971 Da. dev. −1.8 ppm.

1-{1-[3-(6-Fluoro-pyridin-3-yl)-phenyl]-1H-benzoimidazol-5-yl}-ethylamine

This was prepared analogously from 2-(1-{1-[3-(6-fluoro-pyridin-3-yl)-phenyl]-1H-benzoimidazol-5-yl}-ethyl)-isoindole-1,3-dione in 15% yield. LC-ESI-HRMS of [M+H]+ shows 333.1501 Da. Calc. 333.151549 Da. dev. −4.3 ppm.

The major product (24%) from this reaction was

1-{1-[3-(6-Hydrazino-pyridin-3-yl)-phenyl]-1H-benzoimidazol-5-yl}-ethylamine

1-[1-(3-Pyrimidin-5-yl-phenyl)-1H-benzoimidazol-5-yl]-ethylamine

This is prepared analogously from 2-{1-[1-(3-Pyrimidin-5-yl-phenyl)-1H-benzoimidazol-5-yl]-ethyl}-isoindole-1,3-dione.

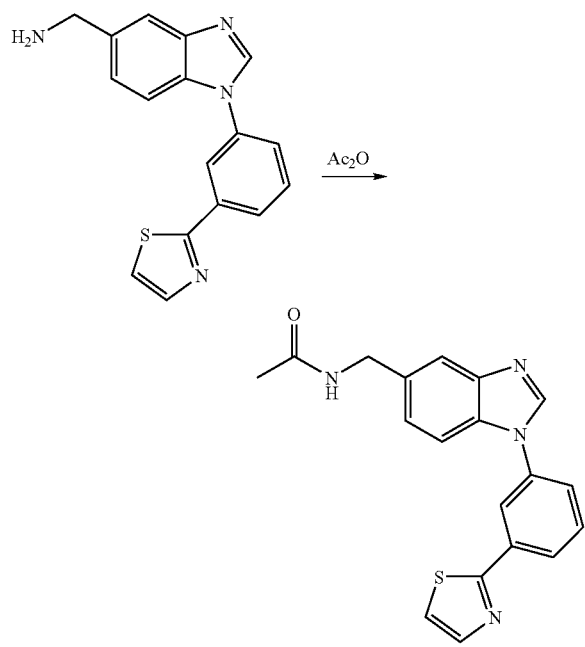

N-[1-(3-Thiazol-2-yl-phenyl)-1H-benzoimidazol-5-ylmethyl]-acetamide

To a suspension of C-[1-(3-thiazol-2-yl-phenyl)-1H-benzoimidazol-5-yl]-methylamine (0.70 g, 2.3 mmol) in dichloromethane (30 ml) was added acetic anhydride (2.4 ml, 2.5 mmol) dropwise with stirring. After the addition, stirring was continued for 30 min and the reaction mixture was washed twice with saturated, aqueous sodium bicarbonate and once with water. The organic phase was dried over sodium sulfate and concentrated in vacuo. The concentrate was purified by column chromatography on silica gel, eluting with a mixture of dichloromethane, methanol and ammonia (9:1:0.1 v/v/v). This afforded the desired product (0.52 g, 65%). Mp. 156.4° C.

N-[1-(3-Pyridin-2-yl-phenyl)-1H-benzoimidazol-5-ylmethyl]-acetamide

This was prepared analogously from C-[1-(3-[pyridin-2-yl]-phenyl)-1H-benzoimidazol-5-yl]-methylamine (0.06 g, 54%). LC-ESI-HRMS of [M+H]+ shows 343.1544 Da. Calc. 343.155886 Da. dev. −4.3 ppm.

Example 2

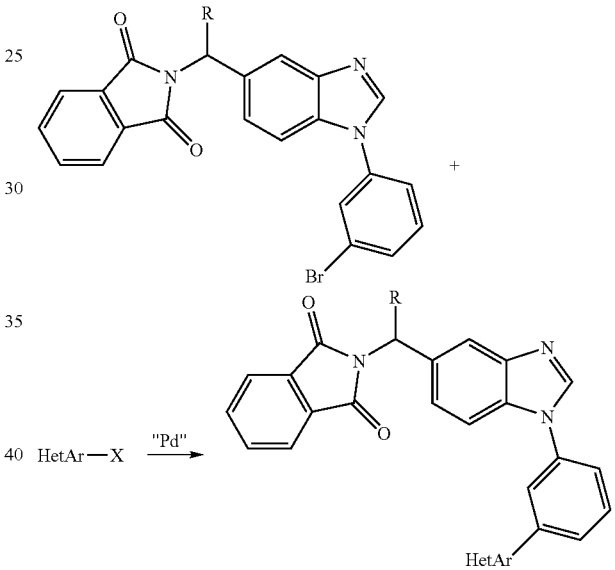

2-[1-(3-(Pyridin-3-yl)-phenyl)-1H-benzoimidazol-5-ylmethyl]-isoindole-1,3-dione A mixture of 2-[1-(3-bromophenyl)-1H-benzimidazol-5-ylmethyl]-isoindole-1,3-dione (1.10 g, 2.54 mmol), 3-pyridineboronic acid (0.47 g, 3.82 mmol), potassium carbonate (1.06 g, 7.63 mmol), 1,3-propanediol (0.92 ml, 12.72 mmol) and dichlorobis(triphenylphosphine)palladium(II) (0.1 g) in a mixture of dimethoxyethane (20 ml) and water (10 ml) was stirred at reflux in a nitrogen atmosphere for 20 min. The resultant mixture was cooled and volatile material was removed in vacuo. The product precipitated from the residual solvent and was filtered off, washed with water and dried in the air to afford 0.56 g.

2-[1-(3-(6-Fluoropyridin-3-yl)-phenyl)-1H-benzoimidazol-5-ylmethyl]-isoindole-1,3-dione This was prepared analogously from 2-[1-(3-bromophenyl)-1H-benzimidazole-5-yl methyl]-isoindole-1,3-dione and (6-fluoro-3-pyridine)boronic acid

2-{1-[1-(3-Pyridin-3-yl-phenyl)-1H-benzoimidazol-5-yl]-ethyl}-isoindole-1,3-dione This was prepared analogously from 2-{1-[1-(3-bromo-phenyl)-1H-benzoimidazol-5-yl]-ethyl}-isoindole-1,3-dione and 3-pyridineboronic acid

2-(1-{1-[3-(6-Fluoro-pyridin-3-yl)-phenyl]-1H-benzoimidazol-5-yl}-ethyl)-isoindole-1,3-dione This was prepared analogously from 2-{1-[1-(3-bromo-phenyl)-1H-benzoimidazol-5-yl]-ethyl}-isoindole-1,3-dione and (6-fluoro-3-pyridine)boronic acid

2-{1-[1-(3-Pyrimidin-5-yl-phenyl)-1H-benzoimidazol-5-yl]-ethyl}-isoindole-1,3-dione This was prepared analogously from 2-{1-[1-(3-bromo-phenyl)-1H-benzoimidazol-5-yl]-ethyl}-isoindole-1,3-dione and 5-pyrimidineboronic acid.

2-[1-(3-(Pyridin-2-yl)-phenyl)-1H-benzoimidazol-5-ylmethyl]-isoindole-1,3-dione To a solution of 2-[1-(3-bromo-phenyl)-1H-benzimidazole-5-ylmethyl]-isoindole-1,3-dione (1.0 g, 2.31 mmol) in anhydrous THF (20 ml) was added 2-tributylstannylpyridine (0.82 ml, 2.54 mmol) and a catalytic amount of tetrakis(triphenylphosphine)palladium(0) (60 mg) and the resultant mixture was stirred at reflux in a nitrogen atmosphere for 3 days. The reaction mixture was quenched with aqueous ammonia and extracted with ethyl acetate. The organic extract was dried over magnesium sulphate and concentrated in vacuo. The concentrate was eluted through silica gel with ethyl acetate to afford the desired product. 0.24 g (24%).

2-[1-(3-(Pyrazin-2-yl)-phenyl)-1H-benzoimidazol-5-ylmethyl]-isoindole-1,3-dione This was prepared analogously from 2-[1-(3-bromo phenyl)-1H-benzimidazole-5-yl methyl]-isoindole-1,3-dione and 2-tri butylstannylpyrazine.

2-[1-[1-(3-(Pyrazin-2-yl)-phenyl)-1H-benzoimidazol-5-yl]-ethyl]-isoindole-1,3-dione This was prepared analogously from 2-{1-[1-(3-bromo-phenyl)-1H-benzoimidazol-5-yl]-ethyl}-isoindole-1,3-dione and 2-tributylstannylpyrazine.

Example 3

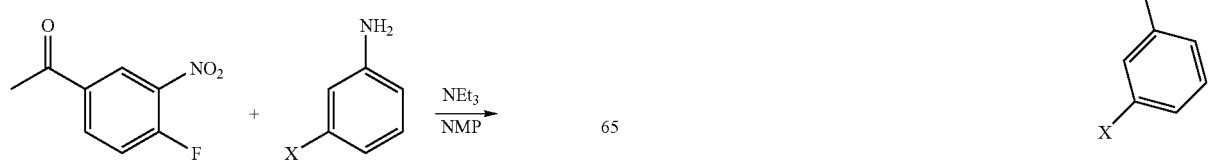

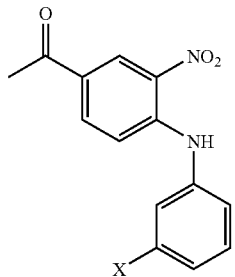

1-[4-(3-Bromo-phenylamino)-3-nitro-phenyl]-ethanone

To a solution of 4-fluoro-3-nitroacetophenone (165 g, 0.9 mol) in NMP (350 ml) was added 3-bromoaniline (98 ml, 0.9 mol) and triethyl amine (125.4 ml, 0.9 mol) and the reaction mixture was stirred at 80° C. for 6 hours and then left with stirring at room temperature over night. The resultant suspension was poured into ice-water and the precipitate was filtered off and washed with water and diethyl ether, successively. Drying in the air afforded the desired product (262g, 87%).

1-{4-[3-(5-Chloro-thiazol-2-yl)-phenylamino]-3-nitro-phenyl}-ethanone

This was prepared analogously from 4-fluoro-3-nitroacetophenone and 3-thiazol-2-yl-phenylamine in 76% yield.

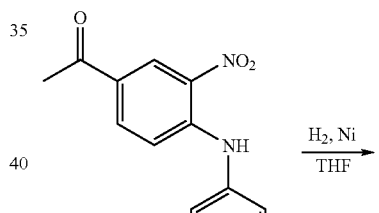

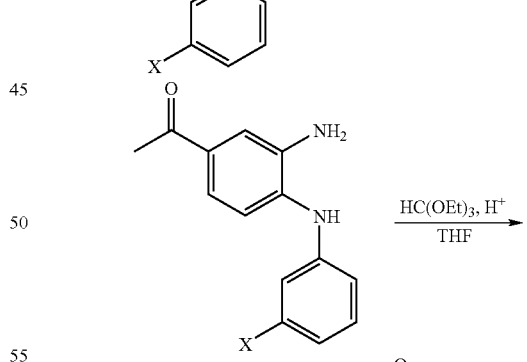

1-[3-Amino-4-(3-bromo-phenylamino)-phenyl]-ethanone

1-[4-(3-Bromo-phenylamino)-3-nitro-phenyl]-ethanone (75 g, 0.22 mol) was dissolved in THF (350 ml) and hydrogenated by standard procedures using Raney nickel as the catalyst to afford the desired diamine, which was used in the next step without further purification.

1-{3-Amino-4-[3-(5-chloro-thiazol-2-yl)-phenylamino]-phenyl}-ethanone

This was prepared analogously from 1-{4-[3-(5-chloro-thiazol-2-yl)-phenylamino]-3-nitro-phenyl}-ethanone.

1-[1-(3-Bromo-phenyl)-1H-benzoimidazol-5-yl]-ethanone

This was prepared from 1-[3-amino-4-(3-bromo-phenylamino)-phenyl]-ethanone (86.5 g, 0.28 mol) by treatment with triethyl orthoformate in THF in the presence of p-toluenesulfonic acid as described in Example 1.

1-{1-[3-(5-Chloro-thiazol-2-yl)-phenyl]-1H-benzoimidazol-5-yl}-ethanone

This was prepared analogously from 1-{3-amino-4-[3-(5-chloro-thiazol-2-yl)-phenylamino]-phenyl}-ethanone.

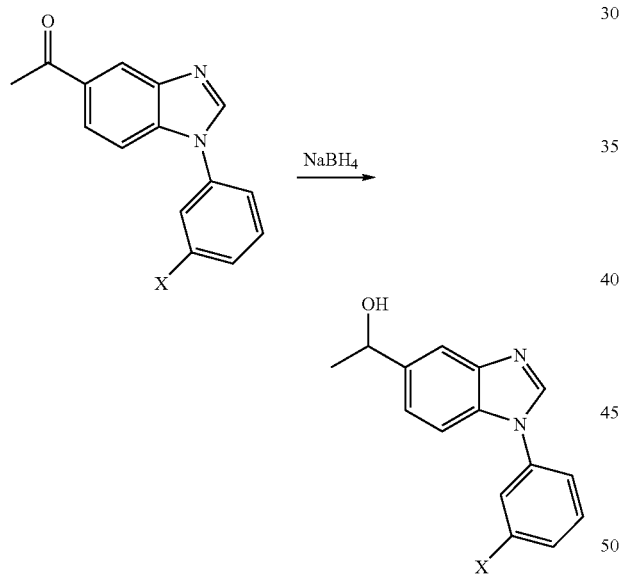

1-{1-[3-(5-Chloro-thiazol-2-yl)-phenyl]-1H-benzoimidazol-5-yl}-ethanol

To a solution of 1-{1-[3-(5-chloro-thiazol-2-yl)-phenyl]-1H-benzoimidazol-5-yl}-ethanone (6.3 g, 17.8 mmol) in methanol (75 ml) was added sodium borohydride (0.91 g, 23.9 mmol) and the resultant mixture was stirred at room temperature in a nitrogen atmosphere for 7 days. The reaction mixture was diluted with four volumes of water and extracted with ethyl acetate. The organic extract was washed with brine, dried over magnesium sulphate and evaporated in vacuo to leave the desired product (4.95 g, 78%). LC-ESI-HRMS of [M+H]+ shows 356.0635 Da. Calc. 356.062436 Da. dev. 3 ppm.

1-[1-(3-Bromo-phenyl)-1H-benzoimidazol-5-yl]-ethanol

This was prepared analogously from 1-[4-(3-bromo-phenylamino)-3-nitro-phenyl]-ethanone.

Example 4

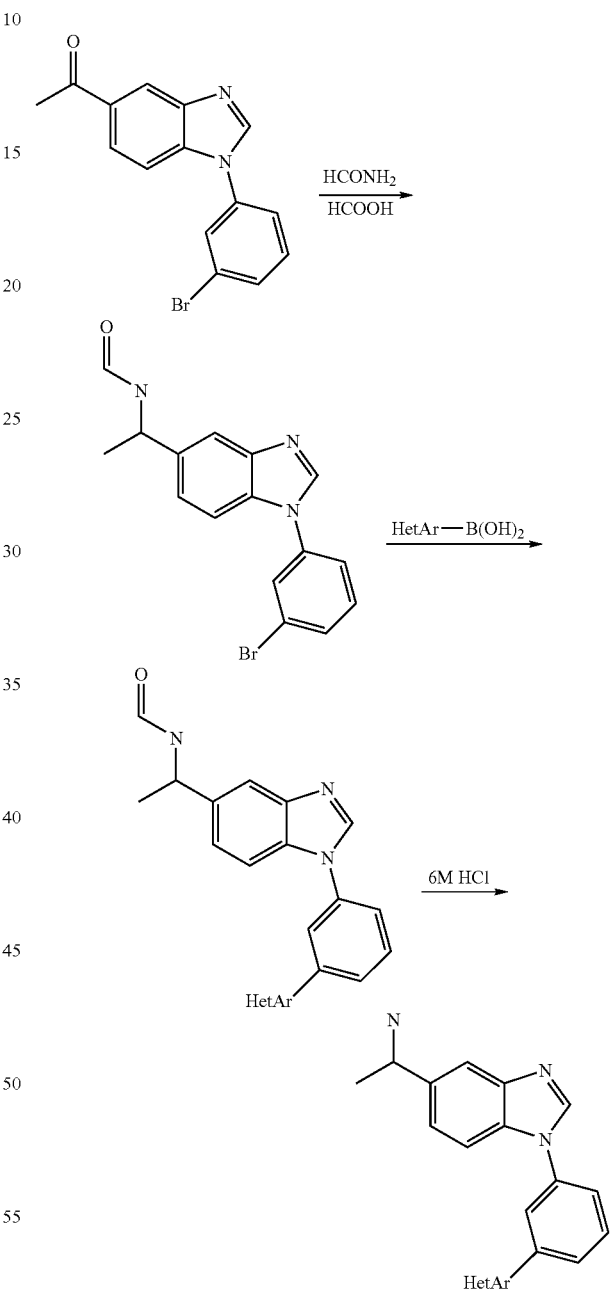

N-{1-[1-(3-Bromo-phenyl)-1H-benzoimidazol-5-yl]-ethyl}-formamide

A mixture of 1-[1-(3-bromo-phenyl)-1H-benzoimidazol-5-yl]-ethanone (7.5 g, 23.8 mmol), formamide (9.5 ml, 23.8 mmol) and formic acid (22.4 ml, 595 mmol) was stirred at 190° C. for 7 hours. The cooled mixture was decanted. The residue was rendered alkaline by addition of saturated, aqueous sodium carbonate and extracted with ethyl acetate. The organic extract was dried over magnesium sulphate and concentrated in vacuo. The concentrate was eluted through silica gel with a mixture of dichloromethane, methanol and aqueous ammonia (9:1:0.1 v/v/v) to afford the desired product (60%).

N-(1-{(1-[3-(2-Fluoro-pyridin-3-yl)-phenyl]-1H-benzoimidazol-5-yl}-ethyl)-formamide To a solution of N-{1-[1-(3-bromo-phenyl)-1H-benzoimidazol-5-yl]-ethyl}-formamide (0.2 g, 0.65 mmol) in a mixture of dimethoxyethane, water and ethanol (4 ml, 7:3:2 v/v/v) was added 2-fluoropyridine-3-boronic acid (0.09 g, 0.65 mmol), bis(triphenylphosphine)-palladium(II) chloride (5 mg) and sodium carbonate (0.07 g, 0.65 mmol) and the resultant mixture was heated to 160° C. by micro wave irradiation for 4 min. The cooled mixture was diluted with ethyl acetate and washed with water. Drying over magnesium sulphate and column chromatographic work-up left the desired product (150 mg, 67%). LC-ESI-HRMS of [M+H]+ shows 361.1451 Da. Calc. 361.146464 Da. dev. −3.8 ppm.

N-(1-{1-[3-(2-Methoxy-pyridin-3-yl)-phenyl]-1H-benzoimidazol-5-yl}-ethyl)-formamide This was prepared analogously from N-{1-[1-(3-bromo-phenyl)-1H-benzoimidazol-5-yl]-ethyl}-formamide and 2-methoxypyridine-3-boronic acid in 77% yield. LC-ESI-HRMS of [M+H]+ shows 373.1666 Da. Calc. 373.166451 Da. dev. 0.4 ppm.

N-(1-{1-[3-(2,4-Dimethoxy-pyrimidin-5-yl)-phenyl]-1H-benzoimidazol-5-yl}-ethyl)-formamide This was prepared analogously from N-{1-[1-(3-bromo-phenyl)-1H-benzoimidazol-5-yl]-ethyl}-formamide and 2,4-dimethoxypyrimidine-5-boronic acid in 81% yield. LC-ESI-HRMS of [M+H]+ shows 404.1729 Da. Calc. 404.172265 Da. dev. 1.6 ppm.

1-{1-[3-(2,4-Dimethoxy-pyrimidin-5-yl)-phenyl]-1H-benzoimidazol-5-yl}-ethylamine A solution of N-(1-{1-[3-(2,4-dimethoxy-pyrimidin-5-yl)-phenyl]-1H-benzoimidazol-5-yl}-ethyl)-formamide (0.53 g, 1.31 mmol) in hydrochloric acid (2.2 ml, 6M) was stirred at 60° C. for 3 hours. To the cooled solution was added ethyl acetate and aqueous sodium carbonate to basic reaction. The layers were separated and the organic layer was dried over magnesium sulphate and concentrated in vacuo. The concentrate was eluted through silica gel with a mixture of dichloromethane, methanol and aqueous ammonia (9:1:0.1 v/v/v) to afford the desired product (0.12 g, 25%). LC-ESI-HRMS of [M+H]+ shows 376.1794 Da. Calc. 376.17735 Da. dev. 5.4 ppm.

1-{1-[3-(2-Methoxy-pyridin-3-yl)-phenyl]-1H-benzoimidazol-5-yl}-ethylamine

This was prepared analogously from N-(1-{1-[3-(2-methoxy-pyridin-3-yl)-phenyl]-1H-benzoimidazol-5-yl}-ethyl)-formamide in 31% yield. LC-ESI-HRMS of [M+H]+ shows 345.1733 Da. Calc. 345.171536 Da. dev. 5.1 ppm.

1-{1-[3-(2-Fluoro-pyridin-3-yl)-phenyl]-1H-benzoimidazol-5-yl}-ethylamine

This is prepared analogously from N-(1-{1-[3-(2-fluoro-pyridin-3-yl)-phenyl]-1H-benzoimidazol-5-yl}-ethyl)-formamide.

Example 5

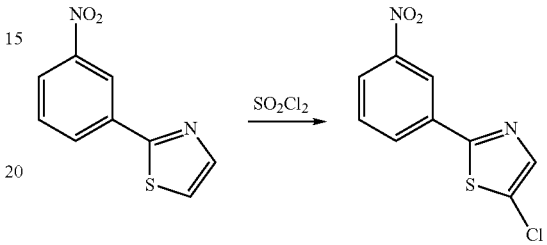

5-Chloro-2-(3-nitro-phenyl)-thiazole

To a stirred solution of 2-(3-nitro-phenyl)-thiazole (18.5 g, 89.7 mmol) in a mixture of chloroform (150 ml) and anhydrous DMF (40 ml) was slowly added sulfuryl chloride (28.2 ml, 359 mmol). After the addition, the resultant mixture was stirred at reflux for 3 hours. The cooled mixture was concentrated under reduced pressure and the residue was partitioned between aqueous calcium chloride (3M) and ethyl acetate. The organic layer was washed with aqueous sodium carbonate, dried over magnesium sulphate and evaporated to dryness to leave the desired product. 20.6 g (80%).

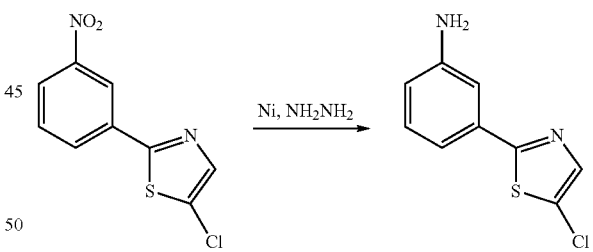

3-Thiazol-2-yl-phenylamine

To a solution of 5-chloro-2-(3-nitro-phenyl)-thiazole (20.0 g, 69.6 mmol) in THF (260 ml) was added hydrazine monohydrate (13.5 ml, 278 mmol) and Raney nickel (2 g). The resultant mixture was stirred at ambient conditions for 1 hour and then filtered through celite. The filtrate was evaporated to dryness and the filtrate was partitioned between ethyl acetate and saturated, aqueous sodium carbonate. The organic layer was dried over sodium sulphate and concentrated in vacuo. The concentrate was eluted through silica gel with a mixture of ethyl acetate and ligroin (1:3 v/v) to afford the desired product (10.6 g, 72%).

Example 6

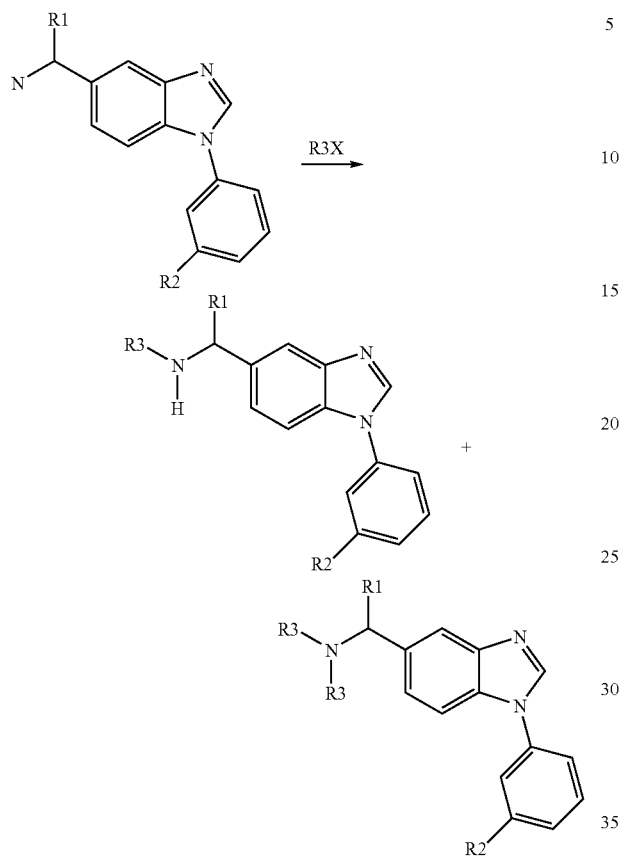

General Procedure:

To a solution of the amine in anhydrous DMF (10-20 ml pr. g of amine) was added 1.1 equivalents of triethyl amine and 1.5 equivalents of the appropriate alkylation agent. The resultant mixture was stirred at room temperature until complete consumption of the starting material (TLC or LC-MS). The mixture was diluted with four volumes of water and extracted with ethyl acetate. Column chromatographic work-up of the concentrated extract afforded the desired products.

By this procedure, the following compounds were prepared:

Methyl-[1-(3-pyridin-3-yl-phenyl)-1H-benzoimidazol-5-ylmethyl]-amine and

Dimethyl-[1-(3-pyridin-3-yl-phenyl)-1H-benzoimidazol-5-ylmethyl]-amine

Mp: 235° C. (as the hydrochloride) from C-[1-(3-pyridin-3-yl-phenyl)-1H-benzoimidazol-5-yl]-methylamine and iodomethane.

Benzyl-{1-[1-(3-pyridin-3-yl-phenyl)-1H-benzoimidazol-5-yl]-ethyl}-amine

LC-ESI-HRMS of [M+H]+ shows 405.2069 Da. Calc. 405.207921 Da. dev. −2.5 ppm.

and

Dibenzyl-{1-[1-(3-pyridin-3-yl-phenyl)-1H-benzoimidazol-5-yl]-ethyl}-amine from 1-[1-(3-Pyridin-3-yl-phenyl)-1H-benzoimidazol-5-yl]-ethylamine Methyl-[1-(3-thiazol-2-yl-phenyl)-1H-benzoimidazol-5-ylmethyl]-amine and Dimethyl-[1-(3-thiazol-2-yl-phenyl)-1H-benzoimidazol-5-ylmethyl]-amine LC-ESI-HRMS of [M+H]+ shows 335.1313 Da. Calc. 335.133042 Da. dev. −5.2 ppm. Prepared from C-[1-(3-Thiazol-2-yl-phenyl)-1H-benzoimidazol-5-yl]-methylamine.

Ethyl-[1-(3-thiazol-2-yl-phenyl)-1H-benzoimidazol-5-ylmethyl]-amine

Mp 224° C. (as the hydrochloride).

and

Diethyl-[1-(3-thiazol-2-yl-phenyl)-1H-benzoimidazol-5-ylmethyl]-amine

Mp. 152° C. (as the hydrochloride).

Benzyl-[1-(3-thiazol-2-yl-phenyl)-1H-benzoimidazol-5-ylmethyl]-amine

LC-ESI-HRMS of [M+H]+ shows 397.1492 Da. Calc. 397.148692 Da. dev. 1.3 ppm.

and

Dibenzyl-[1-(3-thiazol-2-yl-phenyl)-1H-benzoimidazol-5-ylmethyl]-amine

Mp. 126° C.

Example 7

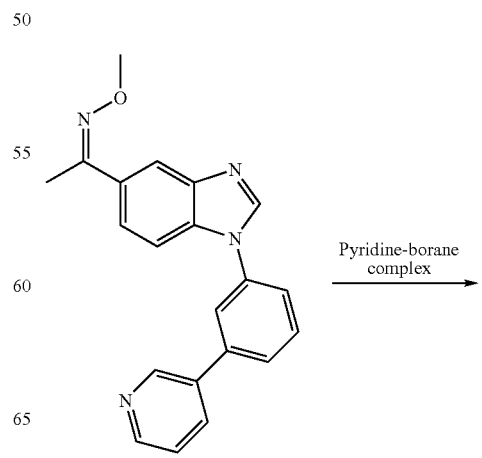

O-Methyl-N-{1-[1-(3-pyridin-3-yl-phenyl)-1H-benzoimidazol-5-yl]-ethyl}-hydroxylamine

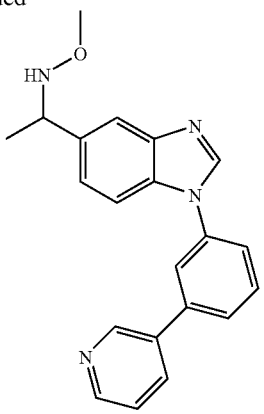

To a solution of 1-[1-(3-pyridin-3-yl-phenyl)-1H-benzoimidazol-5-yl]-ethanone O-methyl-oxime (prepared as described in WO 96/33191) (0.88 g, 2.57 mmol) in dichloromethane (10 ml) was added pyridine-borane complex (0.87 ml, 8.57 mmol) and glacial acetic acid (2.5 ml), successively. The resultant solution was stirred at reflux in a nitrogen atmosphere for 4 days. Hydrochloric acid (5 ml, 1M) was added to the cooled solution and stirring was continued for 30 min and the resultant mixture was concentrated in vacuo. The concentrate was partitioned between ethyl acetate and aqueous sodium bicarbonate. The organic layer was dried over sodium sulphate and eluted through silica gel with a mixture of ethyl acetate and methanol (9:1 v/v). This afforded 27 mg of the desired product. LC-ESI-HRMS of [M+H]+ shows 345.1717 Da. Calc. 345.171536 Da. dev. 0.5 ppm.

Example 8

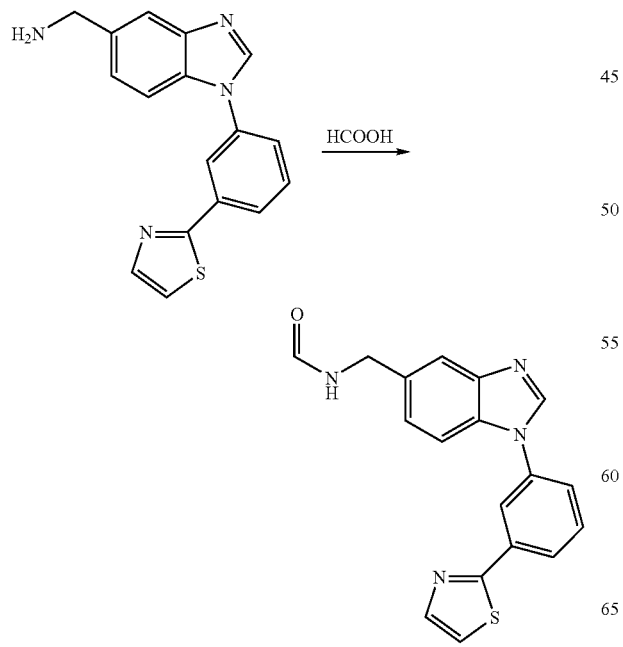

N-{1-[3-(Thiazol-2-yl)-phenyl]-1H-benzoimidazol-5-ylmethyl}-formamide

A solution of C-[1-(3-thiazol-2-yl-phenyl)-1H-benzoimidazol-5-yl]-methylamine (1.4 g, 4.57 mmol) in formic acid (20 ml) was stirred at reflux for 3 hours. The mixture was evaporated in vacuo and the residue was partitioned between ethyl acetate and saturated, aqueous sodium carbonate. The organic layer was dried over magnesium sulphate and concentrated under reduced pressure. The residue was purified by column chromatography on silica gel using a mixture of dichloromethane and methanol (9:1 v/v) as the eluent to afford the desired product 0.5 g (33%). LC-ESI-HRMS of [M+H]+ shows 335.095 Da. Calc. 335.096657 Da. dev. −4.9 ppm.

Example 9

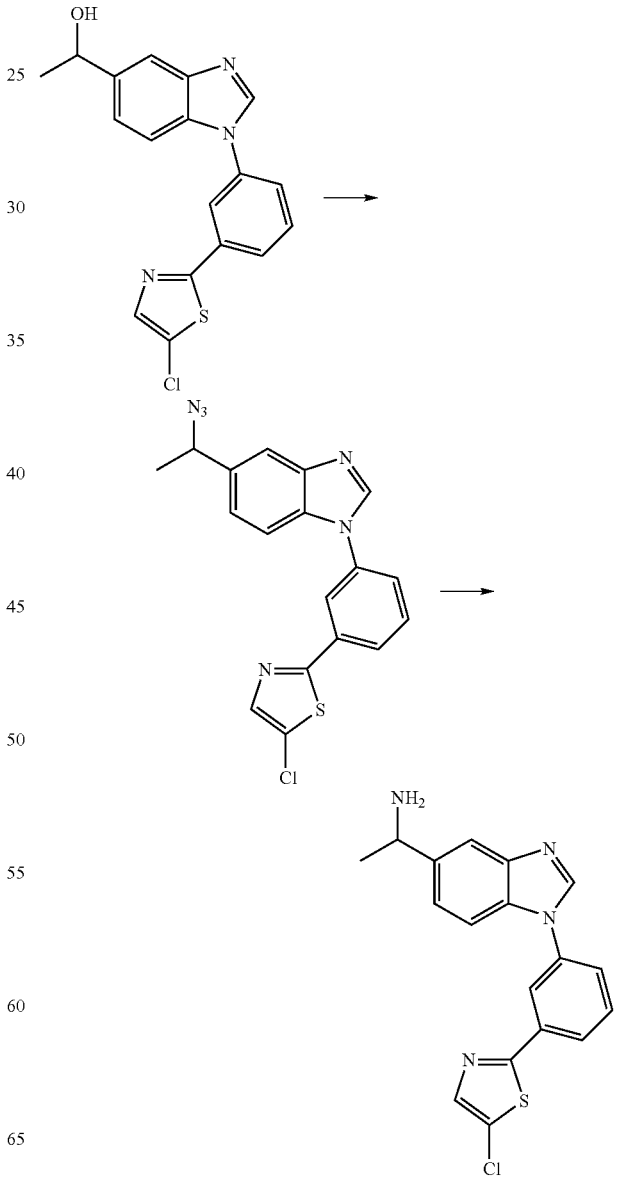

1-{1-[3-(5-Chloro-thiazol-2-yl)-phenyl]-1H-benzoimidazol-5-yl}-ethylamine

A stirred suspension of 1-{1-[3-(5-chloro-thiazol-2-yl)-phenyl]-1H-benzoimidazol-5-yl}-ethanol (1.0 g, 2.80 mmol) in a mixture anhydrous toluene (60 ml) and THF (10 ml) was cooled to 10° C. and 1,8-diazabicyclo[5.4.0]undec-7-ene (0.5 ml, 3.36 mmol) and di-phenylphosphoryl azide (0.95 g, 3.36 mmol) were added, successively. Stirring was continued for 45 min at 10° C., whereafter the temperature was raised and the mixture was stirred at reflux for two days. The cooled mixture was concentrated in vacuo and the concentrate was partitioned between ethyl acetate and saturated, aqueous sodium carbonate. The organic extract was dried over magnesium sulphate, concentrated under reduced pressure and eluted through silica gel with a mixture of dichloro-methane, methanol and aqueous ammonia (9:1:0.1 v/v/v) to afford the desired product (0.75 g, 70%). LC-ESI-HRMS of [M+H]+ shows 355.079 Da. Calc. 355.07842 Da. dev. 1.6 ppm.

Example 10

Some of the amines described in the Examples above, exist as racemic mixtures. The specific enantiomers can be prepared by the general procedure below, starting from the commercially available (R)- and (S)-1-phenylethylamines.

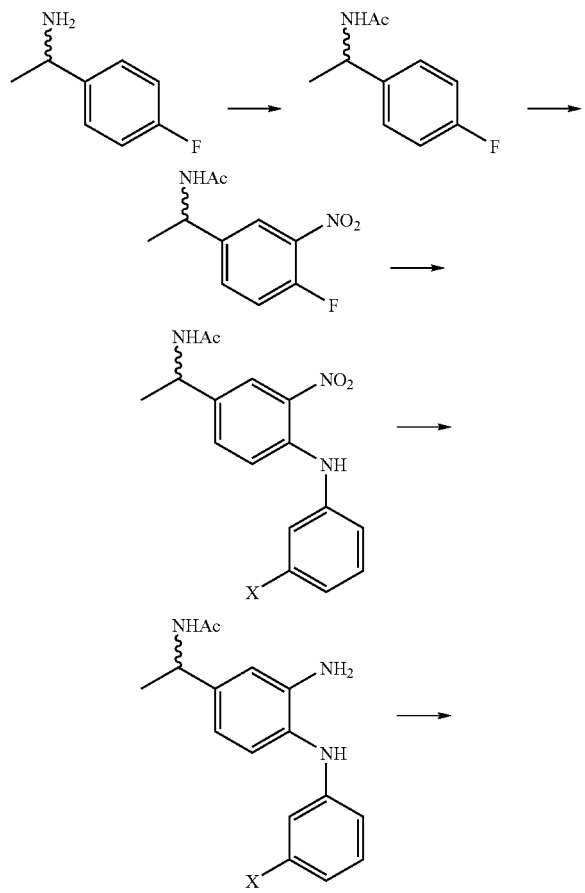

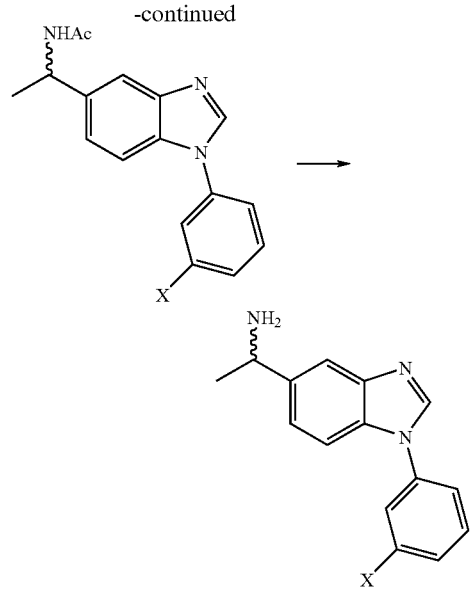

The optically pure 1-(4-fluorophenyl)ethylamine is protected by acetylation with acetic anhydride and nitrated with nitric acid. The resultant product is reacted with the anion of the appropriate formylated 3-substituted aniline to afford a nitroaniline which in turn is hydrogenated and ring-closed.

By this procedure the following compounds are prepared:
(R)-Benzyl-{1-[1-(3-pyridin-3-yl-phenyl)-1H-benzoimidazol-5-yl]-ethyl}-amine and
(S)-Benzyl-{1-[1-(3-pyridin-3-yl-phenyl)-1H-benzoimidazol-5-yl]-ethyl}-amine.
(R)-1-[1-(3-Pyrazin-2-yl-phenyl)-1H-benzoimidazol-5-yl]-ethylamine and
(S)-1-[1-(3-Pyrazin-2-yl-phenyl)-1H-benzoimidazol-5-yl]-ethylamine.
(R)-1-[1-(3-Pyridin-3-yl-phenyl)-1H-benzoimidazol-5-yl]-ethylamine and
(S)-1-[1-(3-Pyridin-3-yl-phenyl)-1H-benzoimidazol-5-yl]-ethylamine.
(R)-1-{1-[3-(6-Hydrazino-pyridin-3-yl)-phenyl]-1H-benzoimidazol-5-yl}-ethylamine and
(S)-1-{1-[3-(6-Hydrazino-pyridin-3-yl)-phenyl]-1H-benzoimidazol-5-yl}-ethylamine.
(R)-1-{1-[3-(6-Fluoro-pyridin-3-yl)-phenyl]-1H-benzoimidazol-5-yl}-ethylamine and
(S)-1-{1-[3-(6-Fluoro-pyridin-3-yl)-phenyl]-1H-benzoimidazol-5-yl}-ethylamine.
(R)-1-[1-(3-Pyrimidin-5-yl-phenyl)-1H-benzoimidazol-5-yl]-ethylamine and
(S)-1-[1-(3-Pyrimidin-5-yl-phenyl)-1H-benzoimidazol-5-yl]-ethylamine.
(R)-1-{1-[3-(5-Chloro-thiazol-2-yl)-phenyl]-1H-benzoimidazol-5-yl}-ethylamine and
(S)-1-{1-[3-(5-Chloro-thiazol-2-yl)-phenyl]-1H-benzoimidazol-5-yl}-ethylamine.
(R)—N-(1-{1-[3(2-Fluoro-pyridin-3yl)phenyl]-1H-benzoimidazol-5-yl}-ethyl)-formamide and
(S)—N-(1-{1-[3-(2-Fluoro-pyridin-3-yl)-phenyl]-1H-benzoimidazol-5-yl}-ethyl)-formamide.
(R)—N-(1-{1-[3-(2-Methoxy-pyridin-3-yl)-phenyl]-1H-benzoimidazol-5-yl}-ethyl)-formamide and
(S)—N-(1-{1-[3-(2-Methoxy-pyridin-3-yl)-phenyl]-1H-benzoimidazol-5-yl}-ethyl)-formamide.
(R) —N-(1-{1-[3-(2,4-Dimethoxy-pyrimidin-5-yl)-phenyl]-1H-benzoimidazol-5-yl}-ethyl)-formamide and (S)—N-(1-{1-[3-(2,4-Dimethoxy-pyrimidin-5-yl)-phenyl]-1H-benzoimidazol-5-yl}-ethyl)-formamide.
(R)-1-{1-[3-(2-Methoxy-pyridin-3-yl)-phenyl]-1H-benzoimidazol-5-yl}-ethylamine and
(S)-1-{1-[3-(2-Methoxy-pyridin-3-yl)-phenyl]-1H-benzoimidazol-5-yl}-ethylamine.
(R)-1-{1-[3-(2,4-Dimethoxy-pyrimidin-5-yl)-phenyl]-1H-benzoimidazol-5-yl}-ethylamine and
(S)-1-{1-[3-(2,4-Dimethoxy-pyrimidin-5-yl)-phenyl]-1H-benzoimidazol-5-yl}-ethylamine.
(R)-1-{1-[3-(2-Fluoro-pyridin-3-yl)-phenyl]-1H-benzoimidazol-5-yl}-ethylamine and
(S)-1-{1-[3-(2-Fluoro-pyridin-3-yl)-phenyl]-1H-benzoimidazol-5-yl}-ethylamine.

TEST METHODS

Test Method 1

In Vitro Inhibition of $^3$H-flunitrazepam ($^3$H-FNM) Binding

The GABA recognition site and the benzodiazepine modulatory unit can selectively be labelled with $^3$H-flunitrazepam.

Tissue Preparation

Preparations are performed at 0-4° C. unless otherwise indicated. Cerebral cortex from male Wistar rats (150-200 g) is homogenised for 5-10 sec in 20 ml Tris-HCl (30 mM, pH 7.4) using an Ultra-Turrax homogeniser. The suspension is centrifuged at 27,000×g for 15 min and the pellet is washed three times with buffer (centrifuged at 27,000×g for 10 min). The washed pellet is homogenized in 20 ml of buffer and incubated on a water bath (37° C.) for 30 min to remove endogenous GABA and then centrifuged for 10 min at 27,000×g. The pellet is then homogenized in buffer and centrifuged for 10 min at 27,000×g. The final pellet is resuspended in 30 ml buffer and the preparation is frozen and stored at −20° C.

Assay

The membrane preparation is thawed and centrifuged at 2° C. for 10 min at 27,000×g. The pellet is washed twice with 20 ml 50 mM Tris-citrate, pH 7.1 using an Ultra-Turrax homogeniser and centrifuged for 10 min at 27,000×g. The final pellet is resuspended in 50 mM Tris-citrate, pH 7.1 (500 ml buffer per g of original tissue), and then used for binding assays. Aliquots of 0.5 ml tissue are added to 25 µl of test solution and 25 µl of $^3$H-FNM (1 nM, final concentration), mixed and incubated for 40 min at 2° C. Non-specific binding is determined using Clonazepam (1 µM, final concentration). After incubation the samples are added 5 ml of ice-cold buffer and poured directly onto Whatman GF/C glass fibre filters under suction and immediately washed with 5 ml ice-cold buffer. The amount of radioactivity on the filters is determined by conventional liquid scintillation counting. Specific binding is total binding minus non-specific binding.

Results 25-75% inhibition of specific binding must be obtained, before calculation of an $IC_{50}$.

The test value will be given as $IC_{50}$ (the concentration (µM) of the test substance which inhibits the specific binding of $^3$H-FNM by 50%).

$IC_{50}$=(applied test substance concentration, $$IC_{50} = \text{(applied test substance concentration, µM)} \times \frac{1}{\left(\frac{C_o}{C_x} - 1\right)}$$

where $C_o$ is specific binding in control assays, and $C_x$ is the specific binding in the test assay.

(The calculations assume normal mass-action kinetics).

Test results from these experiments with a number of compounds of the invention are shown in Table 1 below.

TABLE 1

| Test compound | In vitro binding $IC_{50}$ (µM) |
|---|---|
| C-[1-(3-Thiazol-2-yl-phenyl)-1H-benzoimidazol-5-yl]-methylamine. | 0.011 |
| N-[1-(3-Thiazol-2-yl-phenyl)-1H-benzoimidazol-5-ylmethyl]-acetamide. | 0.024 |
| N-{1-[3-(Thiazol-2-yl)-phenyl]-1H-benzoimidazol-5-ylmethyl}-formamide | 0.0048 |

The invention claimed is:

1. A compound of the general formula (I):

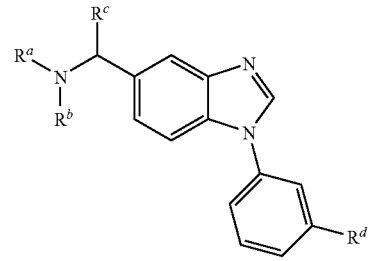

(I)

or an N-oxide thereof, or any of its stereoisomers or any mixture of its stereoisomers, or a pharmaceutically acceptable salt thereof, wherein $R^a$, $R^b$ and $R^c$ independent of each other represent hydrogen, alkyl, cycloalkyl, cycloalkylakyl, alkenyl, alkynyl, hydroxy, alkoxy, alkoxyalkyl, arylalkyl, formyl, alkylcarbonyl or alkoxyalkylcarbonyl;

$R^d$ represents a heteroaryl group;

which heteroaryl group is optionally substituted with one or more substituents independently selected from the group consisting of:

halo, hydroxy, R'R"N—, R'R"N-alkyl, cyano, nitro, trifluoromethyl, trifluoromethoxy, hydrazino, alkoxy, cycloalkoxy, alkyl, cycloalkyl, cycloalkylalkyl, alkenyl, and alkynyl;

wherein R' and R" independent of each other are hydrogen or alkyl.

2. The compound of claim 1, or an N-oxide thereof, or any of its stereoisomers or any mixture of its stereoisomers, or a pharmaceutically acceptable salt thereof, wherein $R^a$ represents hydrogen, alkyl or arylalkyl.

3. The compound of claim 1, or an N-oxide thereof, or any of its stereoisomers or any mixture of its stereoisomers, or a pharmaceutically acceptable salt thereof, wherein $R^b$ represents hydrogen, alkyl, alkoxy, arylalkyl, formyl or alkylcarbonyl.

4. The compound of claim 1, or an N-oxide thereof, or any of its stereoisomers or any mixture of its stereoisomers, or a pharmaceutically acceptable salt thereof, wherein $R^c$ represents hydrogen or alkyl.

5. The compound of claim 1, or an N-oxide thereof, or any of its stereoisomers or any mixture of its stereoisomers, or a pharmaceutically acceptable salt thereof, wherein $R^d$ represents a heteroaryl group selected from thiazolyl, pyridyl, pyrimidyl and pyrazinyl;

which heteroaryl group is optionally substituted with one or more substituents independently selected from the group consisting of:
halo, hydrazino and alkoxy.

6. The compound of claim 1, which is
C-[1-(3-Thiazol-2-yl-phenyl)-1H-benzoimidazol-5yl]-methylamine;
C-[1-(3-Pyridin-3-yl-phenyl)-1H-benzoimidazol-5-yl]-methylamine;
C-[1-(3-[6-Fluoro-pyridin-3-yl]-phenyl)-1H-benzoimidazol-5-yl]-methylamine;
C-[1-(3-[Pyridin-2-yl]-phenyl)-1H-benzoimidazol-5-yl]-methylamine;
C-[1-(3-Pyrazin-2-yl-phenyl)-1H-benzoimidazol-5-yl] methylamine;
1-[1-(3-Pyrazin-2-yl-phenyl)-1H-benzoimidazol-5-yl]-ethylamine;
1-[1-(3-Pyridin-3-yl-phenyl)-1H-benzoimidazol-5-yl]-ethylamine;
1-{1-[3-(6-Fluoro-pyridin-3-yl)-phenyl]-1H-benzoimidazol-5-yl}-ethylamine;
1-{1-[3-(6-Hydrazino-pyridin-3-yl)-phenyl]-1H-benzoimidazol-5-yl}-ethylamine;
1-[1-(3-Pyrimidin-5-yl-phenyl)-1H-benzoimidazol-5-yl] ethylamine;
N-[1-(3-Thiazol-2-yl-pheny)-1H-benzoimidazol-5-ylmethyl]-acetamide;
N-[1-(3-Pyridin-2-yl-phenyl)-1H-benzoimidazol-5-ylmethyl]-acetamide;
N-(1-{1-[3-(2-Fluoro-pyridin-3-yl)-phenyl]-1H-benzoimidazol-5-yl}-ethyl)-formamide;
N-(1-{1-[3-(2-Methoxy-pyridin-3-yl)-phenyl]-1H-benzoimidazol-5-yl}-ethyl)-formamide;
N-(1-{1-[3-(2,4-Dimethoxy-pyrimidin-5-yl)-phenyl]-1H-benzoimidazol-5-yl}-ethyl)-formamide;
1-{1-[3-(2,4-Dimethoxy-pyrimidin-5-yl)-phenyl]-1H-benzoimidazol-5-yl}-ethylamine;
1-{1-[3-(2-Methoxy-pyridin-3-yl)-phenyl]-1H-benzoimidazol-5-yl}-ethylamine;
1-{1-[3-(2-Fluoro-pyridin-3-yl)-phenyl]-1H-benzoimidazol-5-yl}-ethylamine;
Methyl-[1-(3-pyridin-3-yl-phenyl)-1H-benzoimidazol-5-ylmethyl]-amine;
Dimethyl-[1-(3-pyridin-3-yl-phenyl)-1H-benzoimidazol-5-ylmethyl]-amine;
Benzyl-{1- [1-(3-pyridin-3-yl-phenyl)-1H-benzoimidazol-5-yl]-ethyl}-amine;
Dibenzyl-{1-[1-(3-pyridin-3-yl-phenyl)-1H-benzoimidazol-5-yl]ethyl}-amine;
Methyl-[1-(3-thiazol-2-yl-phenyl)-1H-benzoimidazol-5-ylmethyl]amine;
Dimethyl-[1-(3-thiazol-2-yl-phenyl)-1H-benzoimidazol-5-ylmethyl]-amine;
Ethyl-[1-(3-thiazol-2-yl-phenyl)-1H-benzoimidazol-5-yl-methyl]amine;
Diethyl- [1-(3-thiazol-2-yl-phenyl)-1H-benzoimidazol-5-ylmethyl]-amine;
Benzyl-[1-(3-thiazol-2-yl-phenyl)-1H-benzoimidazol-5-ylmethyl]-amine;
Dibenzy-[1-(3-thiazol-2-yl-phenyl)-1H-benzoimidazol-5-ylmethyl]amine;
O-Methyl-N-{1-[1-(3-pyridin-3-yl-phenyl)-1H-benzoimidazol-5-yl]-ethyl}-hydroxylamine;
N-{1-[3-(thiazol-2-yl)-phenyl]-1H-benzoimidazol-5-ylmethyl}-formamide;
1-{1-[3-(5-Chloro-thiazol-2-yl)-phenyl]-1H-benzoimidazol-5-yl}-ethylamine;
or an N-oxide thereof, any of its isomers or any mixture of its isomers,
or a pharmaceutically acceptable salt thereof.

7. A pharmaceutical composition, comprising a therapeutically effective amount of a compound of claim 1, or an N-oxide thereof, any of its stereoisomers or any mixture of its stereoisomers, or a pharmaceutically acceptable salt thereof, together with at least one pharmaceutically acceptable carrier, excipient or diluent.

8. The compound of claim 1, which is 1-{1-[3-(2-Methoxy-pyridin-3-yl)-phenyl]-1 H-benzoimidazol-5-yl}-ethylamine, or an N-oxide thereof, any of its stereoisomers or any mixture of its stereoisomers, or a pharmaceutically acceptable salt thereof.

* * * * *